(12) United States Patent
Kirk et al.

(10) Patent No.: US 9,919,290 B2
(45) Date of Patent: *Mar. 20, 2018

(54) PRODUCTION OF BIOCHAR ABSORBENT FROM ANAEROBIC DIGESTATE

(71) Applicant: CHAR Technologies Inc., Toronto (CA)

(72) Inventors: Donald W. Kirk, Caledon (CA); John W. Graydon, Toronto (CA); Andrew J. White, Breslau (CA)

(73) Assignee: CHAR Technologies Inc., Mississauga (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/176,724

(22) Filed: Jun. 8, 2016

(65) Prior Publication Data

US 2016/0279599 A1  Sep. 29, 2016

Related U.S. Application Data

(63) Continuation of application No. 13/937,675, filed on Jul. 9, 2013, now Pat. No. 9,381,493, which is a continuation of application No. PCT/CA2012/000022, filed on Jan. 12, 2012.

(60) Provisional application No. 61/432,947, filed on Jan. 14, 2011.

(51) Int. Cl.

| | |
|---|---|
| *C01B 31/10* | (2006.01) |
| *B01J 20/20* | (2006.01) |
| *A61M 39/08* | (2006.01) |
| *B09B 3/00* | (2006.01) |
| *B01D 53/04* | (2006.01) |
| *B01J 20/30* | (2006.01) |
| *C05F 17/00* | (2006.01) |
| *B01D 53/02* | (2006.01) |
| *C01B 32/324* | (2017.01) |
| *C01B 32/336* | (2017.01) |
| *C02F 11/04* | (2006.01) |
| *C02F 11/18* | (2006.01) |

(52) U.S. Cl.
CPC .............. *B01J 20/20* (2013.01); *A61M 39/08* (2013.01); *B01D 53/02* (2013.01); *B01D 53/04* (2013.01); *B01J 20/3078* (2013.01); *B01J 20/3085* (2013.01); *B09B 3/0083* (2013.01); *C01B 32/324* (2017.08); *C01B 32/336* (2017.08); *C05F 17/0027* (2013.01); *B01D 2253/102* (2013.01); *C02F 11/04* (2013.01); *C02F 11/18* (2013.01); *Y02C 10/08* (2013.01); *Y02E 50/343* (2013.01); *Y02E 50/346* (2013.01); *Y02P 20/145* (2015.11); *Y02W 10/23* (2015.05); *Y02W 30/43* (2015.05); *Y02W 30/47* (2015.05)

(58) Field of Classification Search
CPC .............. C01B 32/324; C01B 32/336

USPC ........................................................ 502/421
See application file for complete search history.

(56) References Cited

U.S. PATENT DOCUMENTS

| | | | |
|---|---|---|---|
| 4,122,036 A | 10/1978 | Lewis | |
| 4,242,225 A * | 12/1980 | Wolfrum ................ C10B 57/005 | |
| | | | 201/27 |
| 4,263,271 A | 4/1981 | Henning et al. | |
| 5,605,551 A | 2/1997 | Scott et al. | |
| 5,976,373 A | 11/1999 | Trocciola et al. | |
| 6,362,127 B1 | 3/2002 | Khalini et al. | |
| 6,379,527 B1 | 4/2002 | Vogt | |
| 6,962,616 B1 | 11/2005 | Brandosa et al. | |
| 7,524,795 B1 | 4/2009 | Lima et al. | |
| 7,981,835 B2 * | 7/2011 | Srinivasachar .......... B01J 20/20 | |
| | | | 423/460 |
| 8,361,186 B1 | 1/2013 | Shearer et al. | |
| 9,381,493 B2 * | 7/2016 | Kirk ....................... A61M 39/08 | |
| 2006/0014639 A1 | 1/2006 | Bandosz et al. | |
| 2007/0254807 A1 | 11/2007 | Bisque et al. | |
| 2008/0047313 A1 | 2/2008 | Johnson et al. | |
| 2010/0223839 A1 | 9/2010 | Garcia-Perez et al. | |
| 2010/0242351 A1 | 9/2010 | Causer | |

FOREIGN PATENT DOCUMENTS

WO    WO2011097183    8/2011

OTHER PUBLICATIONS

Inguanzo M. et al., "Reactivity of pyrolyzed sewage sludge in air and CO2", Journal of Analytical and Applied Pyrolysis, vols. 58-59, Apr. 1, 2001, pp. 943-954.

(Continued)

*Primary Examiner* — Stuart Hendrickson
(74) *Attorney, Agent, or Firm* — Bereskin & Parr LLP/S.E.N.C.R.L., s.r.l.

(57) ABSTRACT

A novel carbon absorption material is described which is formed from anaerobic digestate. The material has a hollow tubular structure and is particularly advantageous in converting hydrogen sulfide in biogas and in absorbing the converted sulfur and sulfur compounds from biogas into its structure. The material after use as a hydrogen sulfide absorbent has value as a horticultural or agricultural product or as a sulfur impregnated activated carbon. The process for producing this novel carbon absorption material is described. In an embodiment, the process described uses in particular, a humidified inert gas over a temperature range of between about 500° C. to 900° C. to convert anaerobic digestate to an active carbon absorbent. The thermal treatment is relatively mild and retains the fibrous structure of the source material while removing cellulosic and hemicellulosic components from the anaerobic digestate.

11 Claims, 5 Drawing Sheets

(56) References Cited

OTHER PUBLICATIONS

Document relating to European Application No. 12733914.1, dated Jul. 13, 2017 (Extended European Search Report).

* cited by examiner

PRODUCTION OF BIOCHAR ABSORBENT FROM ANAEROBIC DIGESTATE

CROSS-REFERENCE TO RELATED APPLICATION

This application claims the benefit and priority to U.S. patent application Ser. No. 13/937,675 filed on Jul. 9, 2013, which claims the benefit and priority to PCT International Application No. PCT/CA2012/000022 filed on Jan. 12, 2012, which was published in accordance with PCT Article 21(2) on Jul. 19, 2012 in English and which claims the benefit of U.S. Provisional Patent Application No. 61/432,947 filed on Jan. 14, 2011, all of which are incorporated by reference herein.

FIELD OF THE INVENTION

This invention relates to the formation of a novel type of carbonized absorbent which is particularly suitable for removing sulfur contaminants from biogas. The carbonized absorbent after use has value in horticulture and agriculture.

BACKGROUND TO THE INVENTION

The development of non-petroleum sources of fuels is important in long term energy sustainability for most countries. One of these potential sources is from growing biomass and directly or indirectly using the fuel value. A criticism of this approach is that productive farm land may be displaced for these fuel crops. A less controversial source of energy is from wastes produced from agriculture. These materials include animal wastes, food wastes and crop residues. These materials may be used to produce methane using anaerobic digestion technology. Methane is the primary component of Natural Gas and may be substituted for Natural Gas in many applications. Methane when pure is a very clean burning fuel and can be used in vehicles, for heating and when used as the fuel for an engine in an electrical generator can produce electricity. Although there are many potential sources of wastes that could be anaerobically digested, most are not utilized at the present time because of unfavorable economic payback for small-scale systems. One of the significant issues is that the methane produced from anaerobic digestion is not pure but contains substantial amounts of carbon dioxide, an inert gas that dilutes the fuel value of the biogas, and contains contaminants such as sulfur compounds which have an unpleasant odor and cause significant corrosion and environmental emissions. Removal of these sulfur compounds is thus an important step in utilizing biogas.

Many techniques are known for sulfur compound removal from gases. Reactions of the compounds with iron or zinc oxides with or without catalysts, are commonly used in large scale systems where disposal of the reacted products is not a significant issue or cost. Membrane technology is also used in large systems where there is sufficient expertise on staff to maintain the operation. For smaller scale systems water scrubbing and carbon absorption beds have been used. These systems are relatively easy to operate but also produce wastes which require disposal. These wastes typically have significant odor from hydrogen sulfide, a common sulfur compound produced during anaerobic digestion. Hydrogen sulfide is a toxic gas as well as being odorous which complicates the waste disposal.

The production of charcoal from biomaterials is known. The focus was on producing a relatively clean burning solid, a fuel still used in barbecues and cooking stoves. The non-carbon elements are removed by heating the biomaterial in the absence of air and causing the volatilization of these species. More recently, there has been emphasis on converting as much of the biomaterial as possible to volatiles that have fuel value in a process known as pyrolysis. The residual carbon in both cases is somewhat porous but does not have high surface area. For high surface area carbon absorbents, chemical treatment is applied either before pyrolysis or afterwards with a second thermal treatment. This is often followed by a water wash to remove the activating chemical or the unwanted ash.

For activated carbon production, two steps are used. The first produces the elemental carbon and the second activates the carbon. For producing activated carbons with specific absorption characteristics a third step is used in which specific catalytic chemicals are loaded onto the carbon surface. As should be clear, the cost of the activated carbon product increases with the extent of processing required for the final product.

The use of waste materials as a source for activated carbon production is not commonly discussed because the carbon content is relatively low. In an article by Chen et al. ("Physical and Chemical Properties Study of the Activated Carbon made from Sewage Sludge 2002, Waste Management, 22, 755-760) they describe the use of sewage sludge; an anaerobically digested residue from municipal waste water treatment. Zinc chloride was required as an activating agent to enhance the surface area of the carbon product and the carbon content of the activated carbon was only 38.9% C by weight.

The use of anaerobic sludge was also reported to be poor for activated carbon production by Tay et al. In a publication entitled "A Comparative Study of Anaerobically Digested and Undigested Sewage Sludges in Preparation of Activated Carbons" Chemosphere 2001, 44, 53-57, Tay et al. found that the undigested sludge produced an activated carbon with higher carbon content, lower ash content, higher surface area and better phenol adsorption characteristics. Thus the use of digested sludge is discouraged.

Martin et al. ("Feasibility of Activated Carbon Production from Biological Sludge by Chemical Activation with ZnCl2 and H2SO4", Environmental Science and Technology 1996, 17, 667-672) showed that optimal activation conditions produced a surface area of 257 $m^2/g$ with an ash content of 38% and a yield of 34%. This material had a contaminant removal of only 20% of that for a commercial activated carbon. Again this suggests that anaerobic sludge is a poor material for activated carbon production.

In a patent on activated carbons from animal manures (U.S. Pat. No. 7,524,795 issued to Lima et al.) a process is described whereby carbonization of poultry manure followed by activation is used to produce an activated carbon with good metal ion adsorption characteristics. In this work, the starting material is raw poultry manure and not the anaerobic sludge digestate from poultry manure.

A patent by Freel et al. (U.S. Pat. No. 7,199,080) describes how agricultural corn derivatives can be used to produce activated corn carbon. The process involves pyrolysing the corn derivatives to generate carbon char and then activating the char using a steam activation stage. An additional acid washing step is also suggested to remove ash from the product. This process differs from the current process by being a 2 step operation and by starting with raw corn derivatives and not the anaerobically digested solids.

Bandosz et al. (U.S. Pat. No. 6,962,616) teach a process for removing acidic sulfur species from wet gas streams using a carbon absorption material which is produced from dewatered and dried sewage sludge. This process for sewage sludge preparation requires a drying operation, addition of mineral oil and a pyrolyzing step before the carbon material is ready for use as a adsorbent. It will be clear that the current process has advantages over the process of Bandosz et al. in that no mineral oil is required and the starting material is from anaerobic digestate solids and not restricted to sewage sludges. When used for removing acidic sulfur species from a gas stream Bandosz et al. rely on inorganic constituents from the pyrolyzed solids to convert hydrogen sulfide. In claim 3 the authors state that the hydrogen sulfide reacts with the inorganic constituents of the carbon to produce sulfur dioxide or elemental sulfur or salt forms thereof. In the current process for removing hydrogen sulfide from the gas stream there is insufficient inorganic content or chemicals to oxidize the hydrogen sulfide in the gas stream. For the current process a small percentage of oxygen or air should be added to the gas stream and is the oxidant which converts hydrogen sulfide to either sulfur or solid oxidized sulfur compounds. The use of a low percentage of air addition to the gas stream to be cleaned is particularly advantageous in maximizing the capacity of our carbon material for hydrogen sulfide removal. Without this addition, hydrogen sulfide is simply adsorbed and would be a problem for the used absorbent carbon disposal. This is also a problem for commercial activated carbons which can adsorb hydrogen sulfide but are not able to convert hydrogen sulfide to elemental sulfur or oxidized sulfur salts.

The carbon material produced by the current process has the capability of converting essentially all of the hydrogen sulfide in the gas stream to sulfur or oxidized sulfur solids when the gas stream has a few percent air addition. The conversion of hydrogen sulfide to elemental sulfur has a significant advantage in that the used absorbent carbon solids can then be utilized as a secondary value-added product in horticulture or agriculture.

A patent by Beckler and Miller (U.S. Pat. No. 6,277,780) describes preparation of an activated carbon from a variety of carbonaceous sources and a thermal treatment, but in order to make this material suitable as an absorbent the material must be loaded with a phosphorous containing chemical. Clearly simple heat treatment is not sufficient for preparation of a carbon absorbent.

A patent by Khalili et al. (U.S. Pat. No. 6,030,922) describes the preparation of an activated carbon from raw sludge but which requires chemically activating the dried sludge material before thermal treatment. It is clear that this chemical addition is required to produce a useful activated carbon.

A patent by Piskorz et al. (U.S. Pat. No. 5,853,548) describes a two stage process for converting biosolids into fuels and for further heat treating the residual char to produce an activated carbon. In the first stage a temperature range of 390 to 450° C. was used. In the current process, the minimum temperature that was found to be effective was 500° C. A significant difference is that the Piskorz et al. patent has focused on using shredded biomass material rather than anaerobic digestate that is used in the current process. Microbial degradation of biomass in anaerobic digesters reduces the content of readily degradable organic species and hence would reduce the fuel value of the material. The second stage char treatment in the Piskorz et al. patent attempts to minimize the char volume by heating at a temperature of 700° C. for thermal annealing. In the current process, production of an absorbent carbon is the intended product and its minimization is not a desirable goal.

In a patent by Abe et al. (U.S. Pat. No. 5,338,462), a method for decomposing water contaminants such as hydrogen peroxide, hydrazines, quaternary ammonium salts, organic acids and sulfur-containing compounds using an activated carbon is described. The hydrocarbon source material is a nitrogen-rich protein-containing sludge or a waste material comprising microbial proteins or biologically activated sludge. This material is first carbonized at a temperature of from 150° C. to 600° C. then activated at a temperature of from 700° C. to 1,100° C. in an inert gas or a reducing gas atmosphere consisting essentially of steam or gaseous carbon dioxide.

It should be clear that the carbon sources and the end use applications are very different in the Abe et al. patent compared to the current application. The current process claims as a starting material acidogenic digestate which is the fibrous undigested cellulosic and lignin structures from anaerobic digestion of waste materials and not the biologically activated sludge material in the patent by Abe et al. The nitrogen content of our starting material would be poor for the purposes claimed in the patent by Abe et al. and the microbial proteins required by the patent by Abe et al. by would not have the structure required for producing our carbon absorbent.

In a patent by Lewis (U.S. Pat. No. 4,122,036), a process for pyrolysing sewage sludge to produce activated carbon is described. The sewage sludge, which has a high moisture content is mixed with recycled hot char from a rotating kiln to produce a dry, free-flowing product which is fed into the kiln. It is clear that this patent does not teach the conditions required by the current technology for producing a carbon absorbent from anaerobic digestate.

Thus, what is needed is an improved process for producing a carbon absorbent material from anaerobic digestate.

SUMMARY OF THE INVENTION

The current invention addresses a number of the problems as identified further above. More particularly, the invention uses a carbon source (acidogenic digestate) which is available from the anaerobic digestion process, thus avoiding environmental impact of purchasing and using activated carbons produced from coals and petroleum sources.

More particularly, the inventors have developed a novel carbon absorbent material from anaerobic digestate which possesses enhanced activity for cleaning biogas and which creates a valued-added sulfur-containing byproduct after use.

The potential for on-site generation has additional benefits in eliminating transportation green-house gas emissions. The carbon absorbent does not use or require chemical additives such as potassium hydroxide for pore development or activation. The carbon absorbent is produced in a single operation thus simplifying production.

The carbon produced does not simply adsorb hydrogen sulfide from biogas but converts it to a useful form of sulfur and thus creates a useful byproduct rather than a noxious waste material. This property does not require treatment of the carbon with catalysts or chemical additives. As a result of the avoidance of chemical additions, the used carbon can be applied advantageously to horticulture and agricultural operation, thus eliminating any waste generation or disposal problems.

The carbon adsorbent is created without the requirement for chemical additions for pore enhancement or surface activity and is an ecofriendly material for use in horticulture, agriculture or as a generic adsorbent for water or airborne contaminants.

A further object of this invention is to provide a method to produce said carbon absorbent material from anaerobic digestate.

BRIEF DESCRIPTION OF THE DRAWINGS

In order that the invention may be better understood, a preferred embodiment is described, by way of example only, wherein.

DETAILED DESCRIPTION OF THE INVENTION

I. Preparation of the Carbon Absorbent Material

Figure 1:
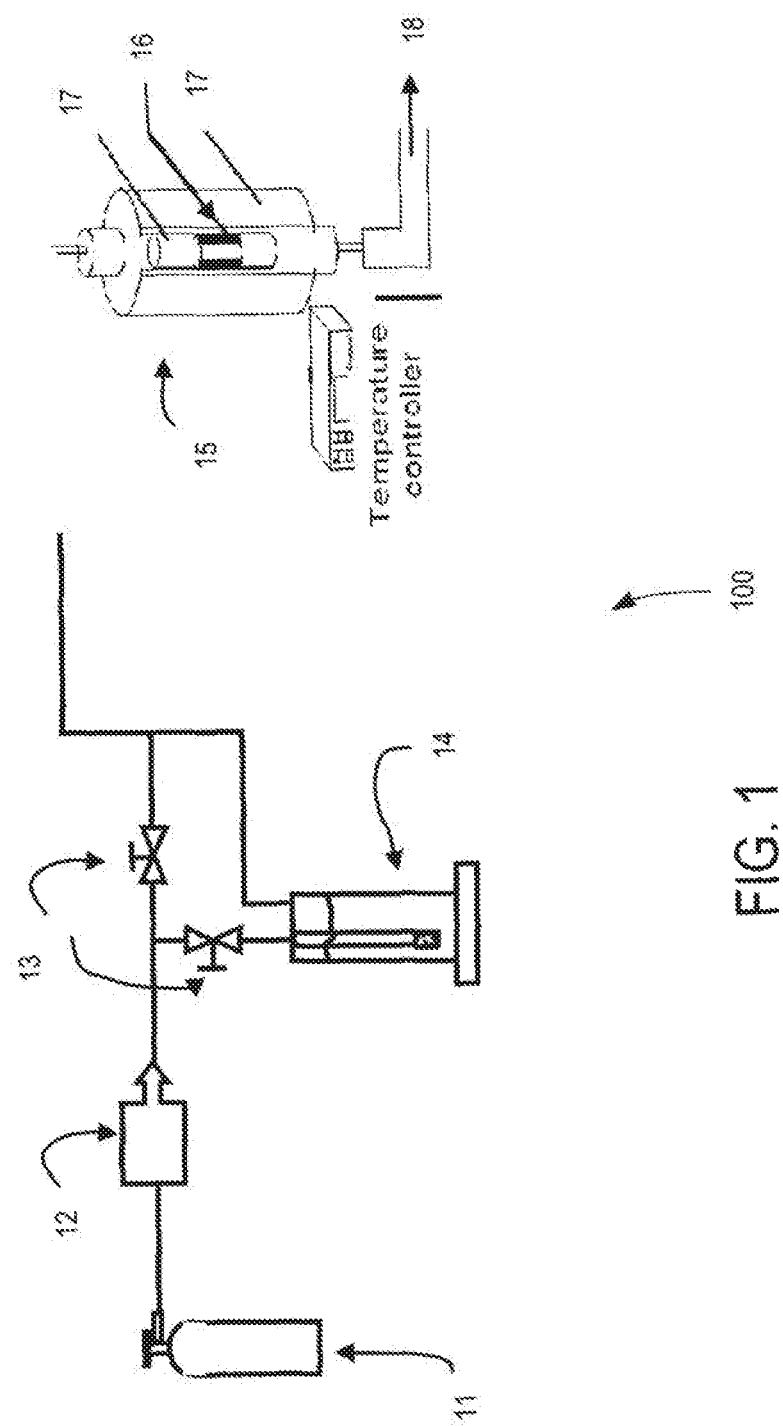
FIG. 1 is a schematic of the apparatus used for heat treating the anaerobic digestate solids.

Samples of anaerobic digestate were obtained from a dairy farm processing animal manure in an anaerobic digester. The solids from the digester were filter pressed then put in piles where the samples were taken. Samples consisting of 30 grams (air dry weight) of material were placed in a quartz tube fitted with a fritted disk to support the samples. The tube was inserted into a tube furnace and inert gas (nitrogen) was directed through the tube. The tube was heated to a temperature set between 400 and 900° C. for 1 hour and then allowed to cool. For some samples, the nitrogen gas was humidified and the temperature of the furnace was set at a temperature between 500 to 850° C. The sample weight after thermal treatment was recorded. A schematic of the apparatus is shown in FIG. 1.

II. Specific Surface Area and Porous Structure Analysis

The measurement of surface area and porous structure was conducted by using a Quantachrome Autosorb Automated Gas Sorption System, surface analyzer (Model SA 3100, Coulter Corp., Miami, Fla.). Nitrogen was selected as the adsorbate for the measurement and helium was chosen as the balancing gas. The adsorption isotherm can be obtained by plotting volume of nitrogen adsorbed against the relative pressure of nitrogen. BET surface area is determined using a BET model.

III. Absorption Capacity

Figure 2:
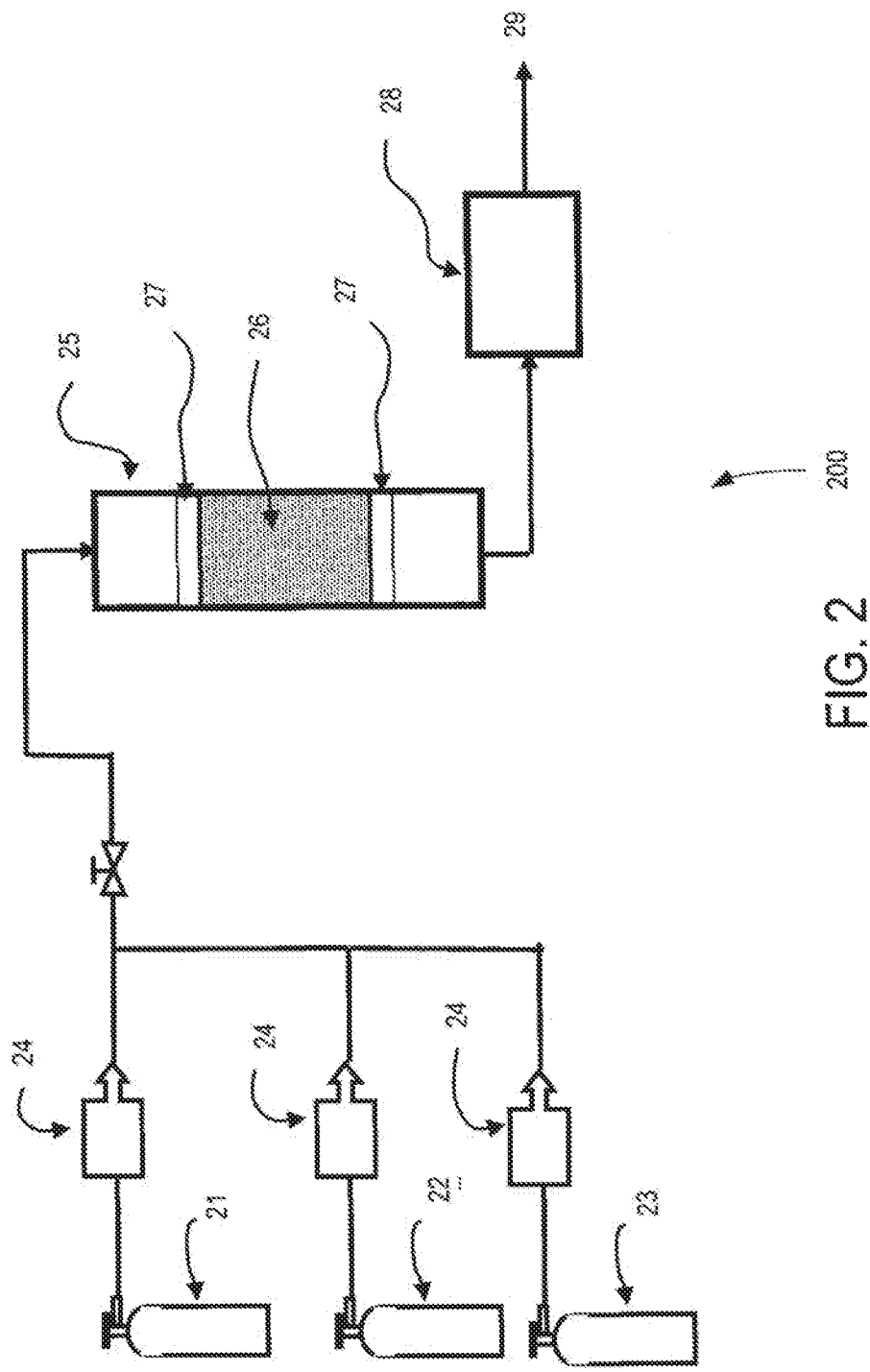
FIG. 2 is a schematic of the apparatus used for the gas absorption measurements.

The capacity of the carbon absorbent was determined using an absorption analysis technique. A schematic of the apparatus is shown in FIG. 2. A weighed sample of the carbon absorbent was placed in a 1.1 cm glass tube with fritted disks above and below the sample. A gas containing various mixtures of carbon dioxide, nitrogen, air, methane, water vapor and hydrogen sulfide were passed through the carbon absorbent material. Flow rates of the gases were controlled using Aalborg mass flow controllers. The concentration of hydrogen sulfide was measured using an Industrial Scientific GasBadge Pro electrochemical gas detector. The time required between the start of hydrogen sulfide flow, which was set to provide a concentration of 450 ppm in the inlet gas mixture into the carbon absorbent, until at least 100 ppm could be measured in the outlet gas composition was recorded. This time is referred to as breakthrough time. The amount of hydrogen sulfide removed from the gas stream during this period per mass of carbon absorbent used in the column was computed and reported as absorption capacity in units of mg of hydrogen sulfide per gram of carbon absorbent. The weight gain of the sample was also measured to confirm the uptake of the hydrogen sulfide.

IV. Analysis of Absorbed Sulfur Species

Figure 5:
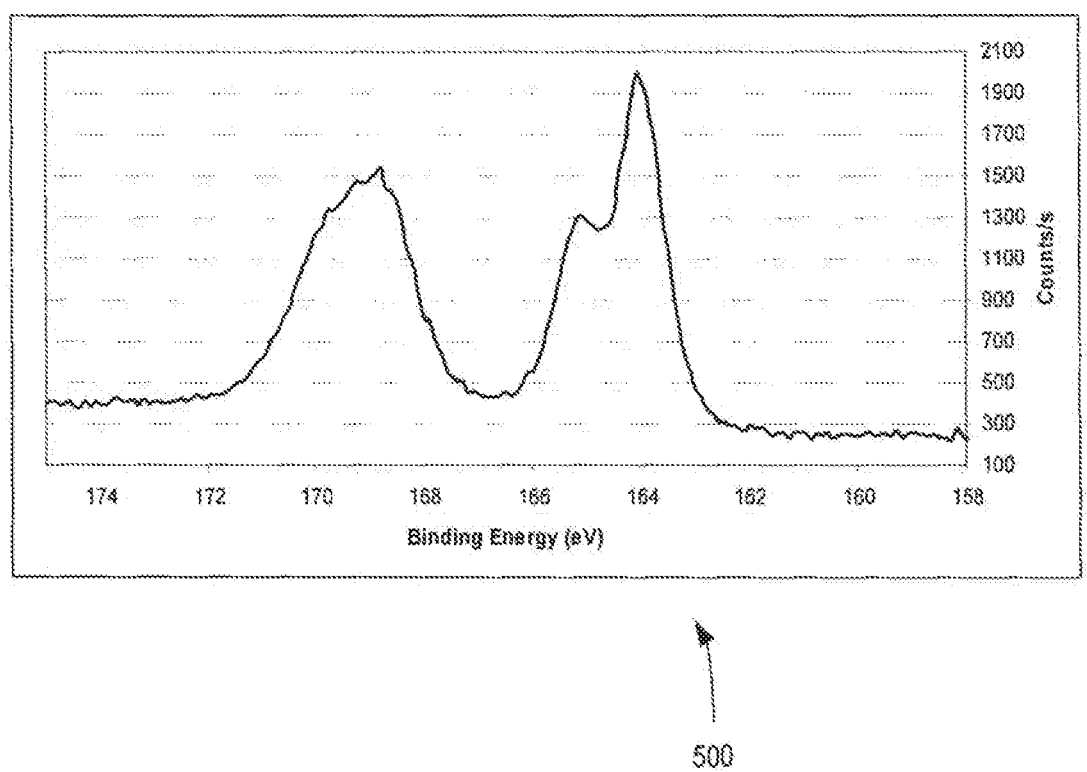
FIG. 5 is an example of the analysis of the sulfur species after the heat treated carbon absorption material has been used for hydrogen sulfide removal.

The determination of the form of sulfur species on the carbon absorbent was conducted using a technique called Xray Photoelectron Spectroscopy (XPS). In this technique, the energy of electrons ejected from the sample irradiated by a monochromatic Al $K_\alpha$ x-ray source was analyzed. The energy of electrons ejected from an irradiated sulfur atom depends on its oxidation state and through correlation with known standards can be determined to be either −2, 0, +4, or +6. An example for the sulfur analysis is shown in FIG. 5

V. Elemental Analysis

The analysis of the elemental composition of the carbon material was conducted using a technique called Inductively Coupled Plasma Atomic Emission Spectroscopy (ICPAES) using a Perkin Elmer model Optima 7300DV ICP AEOS.

VI. Sample Morphology

Figure 3A:
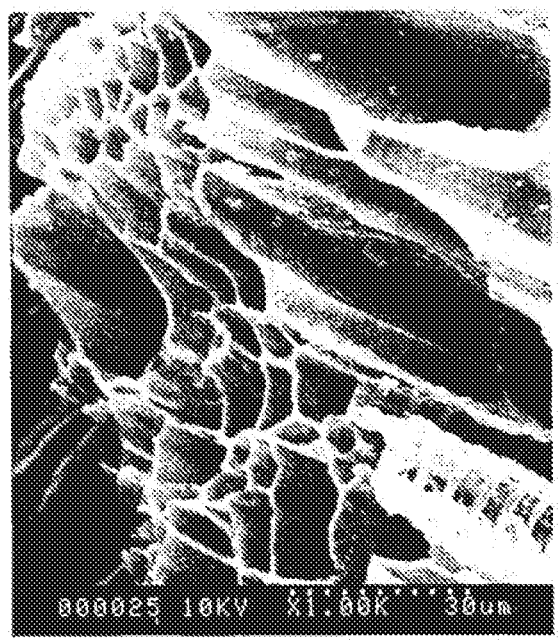
FIGS. 3A and 3B illustrate Scanning Electron Microscopy (SEM) analysis of heat treated anaerobic digestate.
Figure 3B:
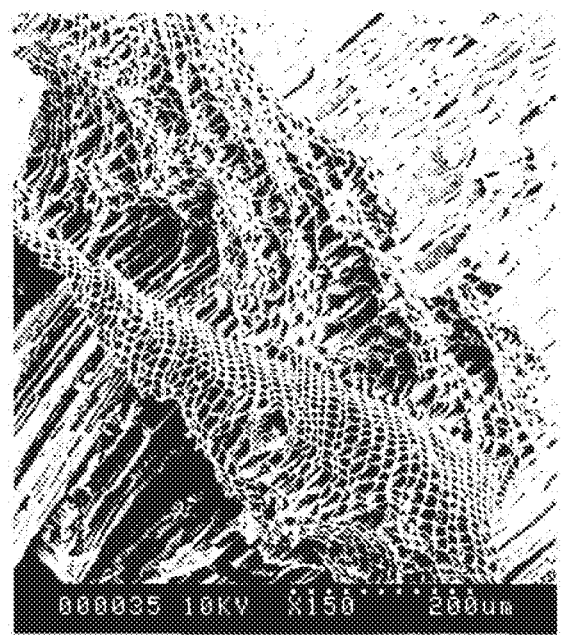

Sample morphology was determined using a technique known as Scanning Electron Microscopy (SEM) as well as optical microscopy. An example of the analysis is shown in FIGS. 3A and 3B.

VII. Digestate Sample Characterization

Figure 4:
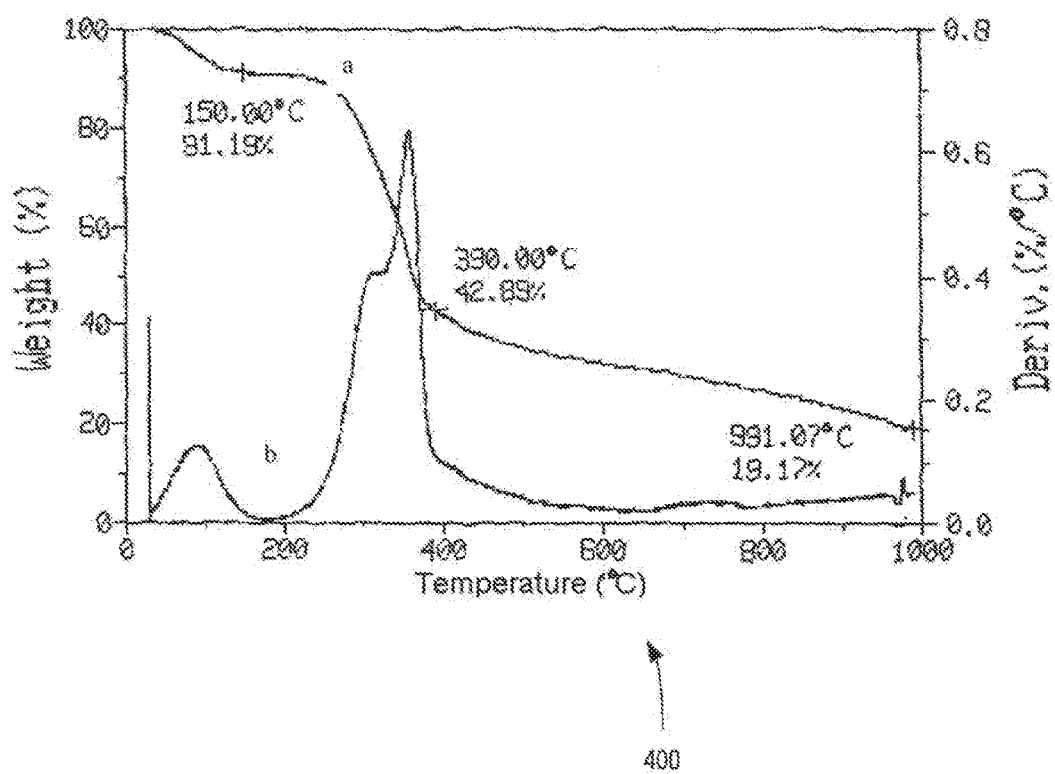
FIG. 4 is an example of the characterization of the anaerobic digestate material using TGA.

The raw digestate samples were characterized using Thermogravimetric Analysis (TGA). In this analysis, a sample is heated in a controlled increasing temperature manner under a nitrogen gas flow while the sample mass is continuously recorded. Loss of mass due to water, cellulose, hemicellulose and lignin were identified at different temperatures. An example of the analysis is shown in FIG. 4.

An illustrative embodiment of the invention will now be described with reference to the figures.

FIG. 1 shows a schematic of the thermal treatment apparatus including an inert gas source (11) such as nitrogen or carbon dioxide or argon or biogas or exhaust combustion gas. Also shown is a mass flow controller (12), such as an Aalborg Gas Mass Flow Controller for inert gas flow rate control. Valves (13) direct gas flow, and in FIG. 1 the valve shown allows the inert gas to be either dry or humidified by directing the gas to a humidifier (14).

Still referring to FIG. 1, in an embodiment, humidifier (14) is a gas bubbler used to force the inert, dry gas to contact water in the vessel. The temperature of the water in the humidifier can be increased to increase the relative humidity of the gas. In an embodiment, the relative humidity may range from about 2% to 95%. More preferably, the relative humidity should be greater than about 10%.

A furnace (15) is shown to provide a heat source, and in an embodiment may be a temperature controllable Carbolite tubular furnace. Although a tube furnace is used in this illustrative example, in principle, any heating apparatus such as fluidized bed, rotating kiln, hearth roaster could be used, provided that the inert gas used has low or no oxygen present. A pyrolysis furnace in which there is no inlet gas flow could also be used, but achieving the beneficial effect of a humidified gas flow would be difficult to achieve.

Still referring to FIG. 1, also shown is an anaerobic digestate sample (16). In this illustrative example, a sample of digestate solids is placed on a fritted disk fitted in a quartz tube. A second fritted disk is placed on top of the sample to ensure there are minimal losses of the sample during heat treatment. A porous quartz fritted disk (17) is used to support the sample, and a second fritted disk is placed on top of the anaerobic digestate sample in order to avoid losses of the digestate solids.

Exhaust gas (18) shown in FIG. 1 contains all the volatile hydrocarbons from the digestate sample, and additionally any carbon-containing compounds produced during the heat treatment. Thus, this exhaust gas (18) may be optimally used as a supplemental fuel for heating the furnace.

Now referring to FIG. 2, shown is a schematic of the apparatus used for determining hydrogen sulfide capacity. For the purpose of demonstration, the gas to be treated (21) was prepared synthetically using pressurized gas from a cylinder. The synthetic gas was doped with hydrogen sulfide contaminant (0-3000 ppm) (22). An additional component was added (air or oxygen at a concentration of 0.01-5 vol % of synthetic gas to be treated). The flow rates were set using mass flow controllers (24) for each gas stream and gases were combined and flowed to the absorption column (25) which held the carbon absorbent (26). A weighed mass of carbon absorbent was held between two fritted disks in the absorption column. The hydrogen sulfide concentration was measured using an Industrial Scientific GasBadge Pro hydrogen sulfide concentration monitor. The treated gas from the absorption column was vented to the atmosphere (29)

EXAMPLES

I. Example 1

The effect of temperature on the anaerobic digestate was tested. Using the experimental set-up shown in FIG. 1, samples of anaerobic digestate solids were taken. A 30 gram (dry weight) sample of material was placed in a quartz tube fitted with a fitted disk to support the sample. The tube was inserted into a tube furnace and inert gas (nitrogen) was directed through the tube. The tube was heated to a temperature set at either 400° C., 500° C. or 700° C. for 1 hour and then allowed to cool. The samples were then tested in the apparatus shown in FIG. 2 to determine their hydrogen sulfide absorption capacity as described. The results showed that the capacities were 0.3 for the 400° C., 2.2 for the 500° C. and 4.1 for the 700° C. in units of mg $H_2S$ per gram of heat treated absorbent carbon. All of these absorbent capacities are low. It is especially clear that treatment at 400° C. for 1 hour does not yield a useful absorbing material.

II. Example II

The beneficial role of oxygen or air addition to a gas to be treated for hydrogen sulfide removal using the absorbent carbon will be demonstrated. Samples of the absorbent carbon produced at 700° C. in Example 1 were tested in the apparatus shown in FIG. 2 to determine hydrogen sulfide absorption capacity. For this test, air was metered using the mass flow meter (24) from a compressed gas cylinder (23) into the gas stream containing hydrogen sulfide to provide a 2% air addition to the gas sent to the absorption column. In this test the break-through time was considerably increased and the capacity at break through was determined to be 35.8 mg $H_2S$ per gram of heat treated absorbent carbon. The dramatic increase in absorption capacity with small additions of an oxidant such as air demonstrates that the absorbent carbon can utilize an external oxidant and does not have to rely on reactive oxygen groups on the carbon surface to interact with hydrogen sulfide.

III. Example 3

The effect of moisture during the heat treatment on the absorption capacity of the absorbent carbon was tested. A sample which had been heat treated as in Example 1 was additionally heated in the presence of humidified nitrogen at a temperature of 850° C. for one hour. The nitrogen gas was humidified by bubbling the gas through water at room temperature before passing into the tube containing the sample. The capacity determined using the procedure used in Example 2 (2% air addition) increased significantly to 177.0 mg $H_2S$ per gram of heat treated absorbent carbon. This capacity increase was so dramatic that the experiment was repeated on three additional samples. The average capacitance value for the four samples was 286.8 mg $H_2S$ per gram of heat treated absorbent carbon. It is clear that the use of a humidified gas flow through the sample during a two stage heat treatment is very important in achieving high absorption capacity.

IV. Example 4

In order to determine whether the humidified heat treatment could be advantageously applied to sample heat treated at other temperatures, four separate samples were heat treated at 500° C. for one hour then were additionally heated in the presence of humidified nitrogen at a temperature of 850° C. for one hour. For these samples the average capacity was 407.4 mg $H_2S$ per gram of heat treated absorbent carbon. Again the second stage of humidified gas treatment increased the capacitance in a very significant manner.

In order to determine whether the humidification could be conducted in a single temperature treatment step, a sample was heat treated for one hour at 850° C. with humidified nitrogen gas. In this example, the heat treated sample had a capacitance of 330 mg $H_2S$ per gram of heat treated absorbent carbon. Thus, the beneficial effect of humidifying the inert gas passing through the sample at the heat treatment temperature is demonstrated. Single heat treatment processes have a numerous benefits over two stage treatments in terms of capital and operating costs and processing time.

V. Example 5

The cause of the very high absorption capacity of the thermally treated samples was investigated using SEM as described earlier. FIG. 3 shows a highly magnified view of the absorbent carbon. The morphology clearly shows carbonized hollow fiber tubes. Thus the fibrous nature of the raw digestate has been retained after the thermal treatment. The structure appears to be unique and may be the cause of the high absorption capacity.

VI. Example 6

The nature of the anaerobic digestate which leads to the formation of the absorbent carbon through the thermal heat treatment was investigated using Thermal Gravimetric Analysis as described earlier. FIG. 4 shows a thermogram of the response of a sample being heated at 10° C. per minute to a temperature of 950° C. The weight loss curve (a) begins at a normalized initial sample weight of 100%. As the temperature rises, volatile species are lost and the weight decreases. Different species have different volatilization temperatures. For example, the weight loss beginning at 100° C. is due to evaporation of residual water. The temperature regions for loss of different species is more easily identified by plotting the rate of weight loss (curve b) as a function of temperature. For this curve, there is a peak at 150° C. representing the loss of water starting at 100° C. and being complete by about 180° C. There are two other overlapping peaks at about 325° C. and 390° C. which represent the loss of hydroxyl groups from hemicellulose and cellulose. At higher temperatures there is a slow, continuing loss of weight likely due to lignin degradation. The results clearly indicate that at the thermal temperatures used for anaerobic digestate treatment, water, and then the hydroxyl groups from hemicellulose and cellulose should be fully removed from the sample. The relatively gentle thermal conditions are likely responsible for retaining the fiber structure in the treated samples seen in FIG. 3.

VII. Example 7

The nature of the hydrogen sulfide absorption on the carbon absorbent was analyzed using XPS as described earlier. FIG. 5 shows the XPS spectrum of the sulfur found on a humidified, heat treated, absorbent carbon after hydrogen sulfide absorption. There are two prominent peaks corresponding to sulfur oxidation states of 0 and +6. There is no evidence of a peak between 161 and 162 eV which would represent hydrogen sulfide. Thus the analysis shows that the carbon absorbent produced converts hydrogen sulfide to higher oxidation states and avoids any odor issues by eliminating hydrogen sulfide entirely.

Thus, in an aspect, there is provided a carbon absorbent material produced from anaerobic digestate (acidogenic digestate) through heat treatment at greater than or equal to 500° C., which remains structurally intact despite losing the hydroxyl groups of the cellulose and hemicellulose and which retains its non-hydrocarbon elements.

In an embodiment, a carbon absorbent material produced from anaerobic digestate of animal manures through heat treatment with a humidified gas at greater than or equal to 500° C. which remains structurally intact despite losing the hydroxyl groups of its cellulose and hemicellulose content and retains its non-hydrocarbon elements.

In another aspect, there is provided a process for producing a carbon absorbent material which comprises all or some steps of:
a. Feeding dewatered anaerobic digestate into a vessel (thermal reactor) which is heated to a temperature of 500° C.;
b. Passing humidified non-combustible gas through the sample in the reactor for greater for a period of 30 minutes or longer
c. Withdrawing the heat treated carbon from said reactor.
d. Removing sulfur contaminants from a gas stream by passing said gas stream, to which a small percentage of air or oxygen (0.01% to 5%) has been added, through the heat treated carbon to allow absorption and reaction of the sulfur species with the absorbent carbon.
e. Removal of the absorbent carbon for use as a horticultural, agricultural product or for use as a sulfur impregnated activated carbon.
f. Using the heat treated carbon directly after step c as a horticultural, agricultural product or for use as an activated carbon.

In an embodiment, the carbon absorption material is from anaerobic digestate from animal manure.

In another embodiment, the temperature of the vessel (thermal reactor) is from 500° C.-900° C., and more preferably at or around 850° C.

In another embodiment, the gas is humidified nitrogen, carbon dioxide, exhaust gas from a combustion process, anaerobic digestion gas.

In another embodiment, the thermal treatment time is preferably between 30 minutes and 3 hours, and more preferably around 1 hour.

In another embodiment, the process is a two step process: a dry gas thermal treatment at 500° C. or greater, followed by a humidified gas treatment at or around 850° C.

In another embodiment, the exit gas from the reactor is used as a supplemental fuel for providing heat for the thermal reactor.

In another aspect, there is provided a method for producing a carbon absorbent material from anaerobic digestate, comprising: feeding dewatered anaerobic digestate into a thermal reactor which is heated to a temperature of at least 500° C.; passing humidified gas through the anaerobic digestate in the thermal reactor for a period of at least 30 minutes; and withdrawing heat treated absorbent carbon after cooling from the thermal reactor.

In an embodiment, the anaerobic digestate comprises one or more of animal manures and agricultural wastes.

In another embodiment, the anaerobic digestate comprises animal manures processed into heat treated absorbent carbon which remains structurally intact despite losing hydroxyl groups of its cellulose and hemicellulose content.

In another embodiment, the temperature of the thermal reactor ranges from 500° C. to 900° C.

In another embodiment, the temperature of the thermal reactor is at or around 850° C.

In another embodiment, the humidified gas is one or more of nitrogen, carbon dioxide, exhaust gas from a combustion process, and anaerobic digestion gas.

In another embodiment, the method further comprises humidifying the gas to a relative humidity in a range between 2% and 95%.

In another embodiment, the relative humidity of the gas is greater than 10%.

In another embodiment, passing the humidified gas through the anaerobic digestate in the thermal reactor ranges for a period of 30 minutes to 3 hours.

In another embodiment, the humidified gas through the anaerobic digestate in the thermal reactor proceeds for between 45 and 75 minutes.

In another embodiment, passing the humidified gas through the anaerobic digestate in the thermal reactor proceeds for about 60 minutes.

In another aspect, the method comprises providing a dry gas thermal treatment at 500° C.; and providing a humidified gas treatment between 800° C. and 900° C.

In another embodiment, the humidified gas treatment is completed at around 850° C.

In another embodiment, the method further comprises using the exit gas from the reactor as a supplemental fuel for generating heat for the thermal reactor.

In another embodiment, the method further comprises using the absorbent carbon produced, to remove gaseous contaminants such as hydrogen sulfide or organic sulfur containing species from anaerobic digestion gas, landfill gas by adding air or oxygen at a concentration of 0.01% to 5% to gas to be cleaned and passing the mixture through a bed of absorbent carbon.

In another embodiment, the method further comprises using the heat treated absorbent carbon which has been used for removing hydrogen sulfide or organic sulfur containing species from anaerobic digestion gas, landfill gas as a horticultural, agricultural product or as a sulfur impregnated activated carbon.

In another embodiment, the method further comprises using the heat treated absorbent carbon directly as a horticultural, agricultural product for retaining moisture and nutrients in soils.

Although this disclosure has described and illustrated certain preferred embodiments of the invention, it should be pointed out that the invention is not restricted to those particular embodiments. The embodiments of the invention in which an exclusive property or privilege is claimed are defined in the claims.

The invention claimed is:

1. A method of producing a carbon absorbent material, the method comprising:
   providing a quantity of carbon source;
   heating the quantity of carbon source to at least 400° C.;
   humidifying a flow of activation gas to a relative humidity of between 2% and 95%;
   after said heating, activating the carbon source thereby producing activated carbon by directing the flow of activation gas into contact with the quantity of carbon source; and
   using exhaust gas to fuel heating of carbon source, the exhaust gas being the flow of activation gas after contacting the quantity of carbon source and including volatile hydrocarbons captured from the quantity of carbon source.

2. The method of claim 1, wherein:
the carbon source comprises biomass.

3. The method of claim 1, wherein:
the carbon source comprises anaerobic digestate.

4. The method of claim 1, wherein:
said humidifying comprises humidifying the flow of activation gas to a relative humidity of at least 10%.

5. The method of claim 1, wherein:
using the exhaust gas to fuel heating of carbon source comprises using the exhaust gas to fuel the heating of the quantity of carbon source.

6. The method of claim 1, wherein:
using the exhaust gas to fuel heating of carbon source comprises using the exhaust gas to fuel heating of another quantity of carbon source.

7. The method of claim 1, further comprising:
removing substantially all moisture, and hydroxyl groups from hemicellulose and cellulose from the quantity of carbon source by the heating.

8. The method of claim 1, wherein:
the carbon source comprises one or more of animal manure, agricultural waste, and food waste.

9. The method of claim 1, wherein:
the flow of activation gas is one of a flow of nitrogen gas, and a flow of carbon dioxide gas.

10. The method of claim 1, further comprising:
forming a porous open structure in the carbon source.

11. The method of claim 10, wherein:
forming the porous open structure comprises forming a carbonized hollow tubular structure in the carbon source.

* * * * *